United States Patent [19]
Esrock

[11] Patent Number: 5,460,619
[45] Date of Patent: Oct. 24, 1995

[54] DISPOSABLE TUBULAR DEVICE AND METHOD

[76] Inventor: Bernard S. Esrock, 320 Dungate Dr., Chesterfield, Mo. 63017

[21] Appl. No.: 222,109

[22] Filed: Apr. 4, 1994

[51] Int. Cl.[6] .................................................. A61C 17/00
[52] U.S. Cl. ....................................... 604/280; 433/80
[58] Field of Search ......................... 604/280, 264, 604/257, 258, 261; 433/80, 88, 126, 127

[56] References Cited

U.S. PATENT DOCUMENTS

| | | | |
|---|---|---|---|
| 601,564 | 3/1898 | Gurnee . | |
| 661,167 | 11/1900 | Cole . | |
| 828,722 | 8/1906 | Dorment . | |
| 911,646 | 2/1909 | Cook et al. . | |
| 2,564,400 | 8/1951 | Hall | 128/173 |
| 3,137,297 | 6/1964 | Maurer et al. | 128/173.1 |
| 3,254,646 | 6/1966 | Staunt et al. | 128/224 |
| 3,375,823 | 4/1968 | Pamplin et al. | 128/173.1 |
| 3,391,696 | 7/1968 | Woodward | 128/232 |
| 3,401,691 | 9/1968 | Beu | 128/173.1 |
| 3,488,849 | 1/1970 | Lieb et al. | 32/22 |
| 3,570,483 | 3/1971 | Stram | 128/173.1 |
| 3,581,399 | 6/1971 | Dragan | 32/60 |
| 3,647,143 | 3/1972 | Gauthier et al. | 239/342 |
| 3,698,088 | 10/1972 | Austin, Jr. | 32/22 |
| 3,874,083 | 4/1975 | Buckley | 32/22 |
| 3,968,796 | 7/1976 | Baker | 128/173.1 |
| 4,026,025 | 5/1977 | Hunt | 32/22 |
| 4,149,315 | 4/1979 | Page, Jr. et al. | 32/22 |
| 4,248,589 | 2/1981 | Lewis | 433/80 |
| 4,249,899 | 2/1981 | Davis | 433/32 |
| 4,676,749 | 6/1987 | Mabille | 433/88 |
| 4,975,054 | 12/1990 | Esrock | 433/80 |
| 4,984,984 | 1/1991 | Esrock | 433/88 |
| 5,049,071 | 9/1991 | Davis et al. | 433/80 |
| 5,167,623 | 12/1992 | Cianci et al. | 604/43 |
| 5,192,206 | 3/1993 | Davis et al. | 433/80 |
| 5,236,356 | 8/1993 | Davis et al. | 433/80 |
| 5,284,687 | 2/1994 | Blemberg | 428/35.2 |

*Primary Examiner*—John D. Yasko
*Assistant Examiner*—Manuel Mendez
*Attorney, Agent, or Firm*—Senniger, Powers, Leavitt & Roedel

[57] ABSTRACT

A disposable tubular device adapted for releasable and sealing connection to a medical instrument for transporting fluid between a patient and the instrument comprises a generally pliable elongate tube of resilient material extending substantially the entire length of the device and a tube-support structure extending substantially the entire length of the tube. The medical instrument has a nipple with a fluid passageway therethrough and the tube has a proximal end configured to be slidably pushed onto the nipple of the medical instrument to a position in which the nipple fits snugly inside the proximal end of the tube. The tube further comprises a distal end and an elongate fluid passageway extending through the tube from its proximal end to its distal end. The fluid passageway is configured to communicate with the fluid passageway of the nipple when the proximal end of the tube is on the nipple. The tube is sufficiently pliable to expand radially outwardly at its proximal end when the proximal end is pushed on the nipple and sufficiently resilient to form a continuous seal around the nipple for sealing against fluid leakage between the nipple and the tube when fluid flows through the passageways. The tube-support structure has a stiffness greater than that of the tube and sufficient to maintain the tube in a selected operative position.

26 Claims, 2 Drawing Sheets

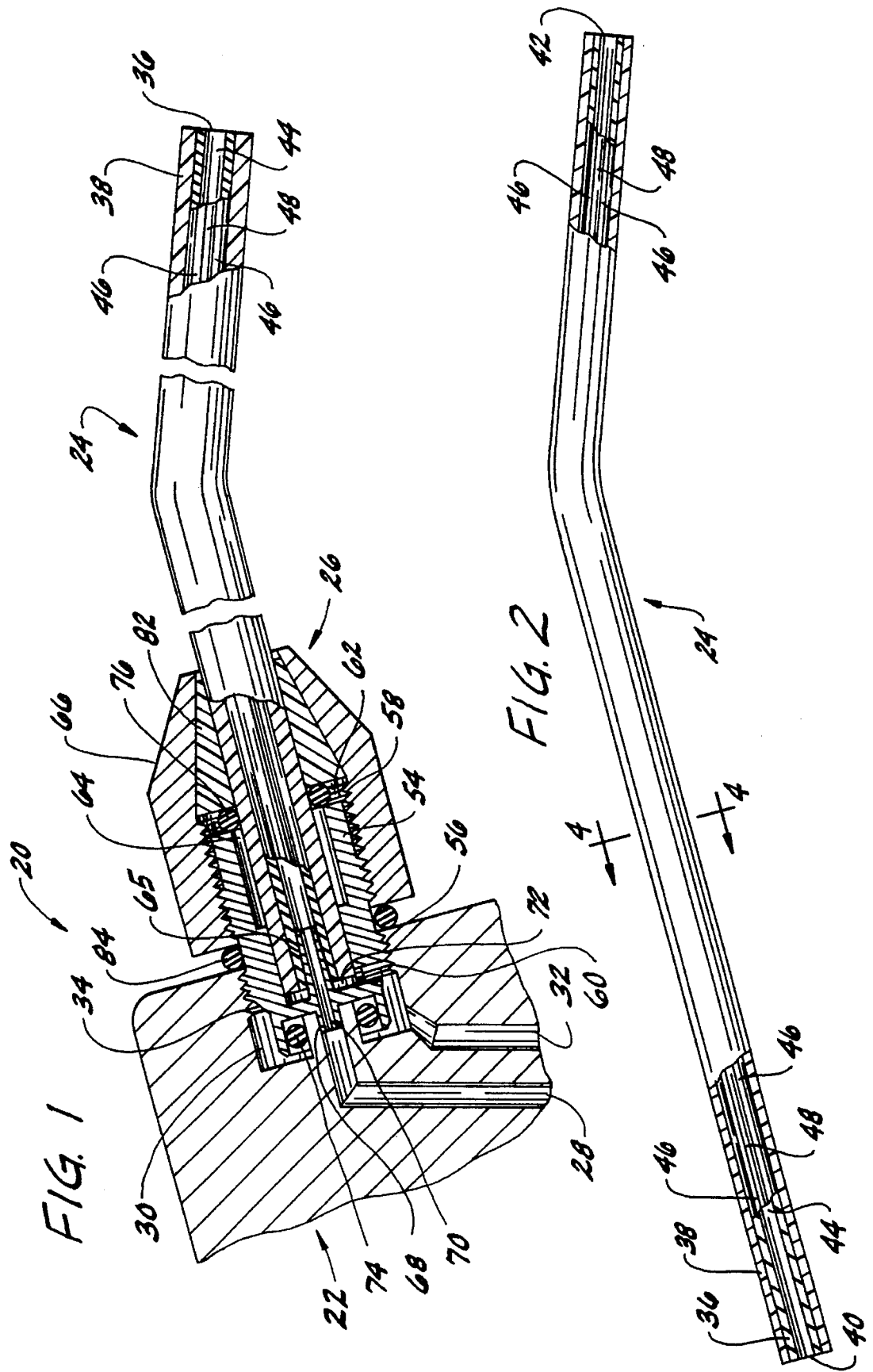

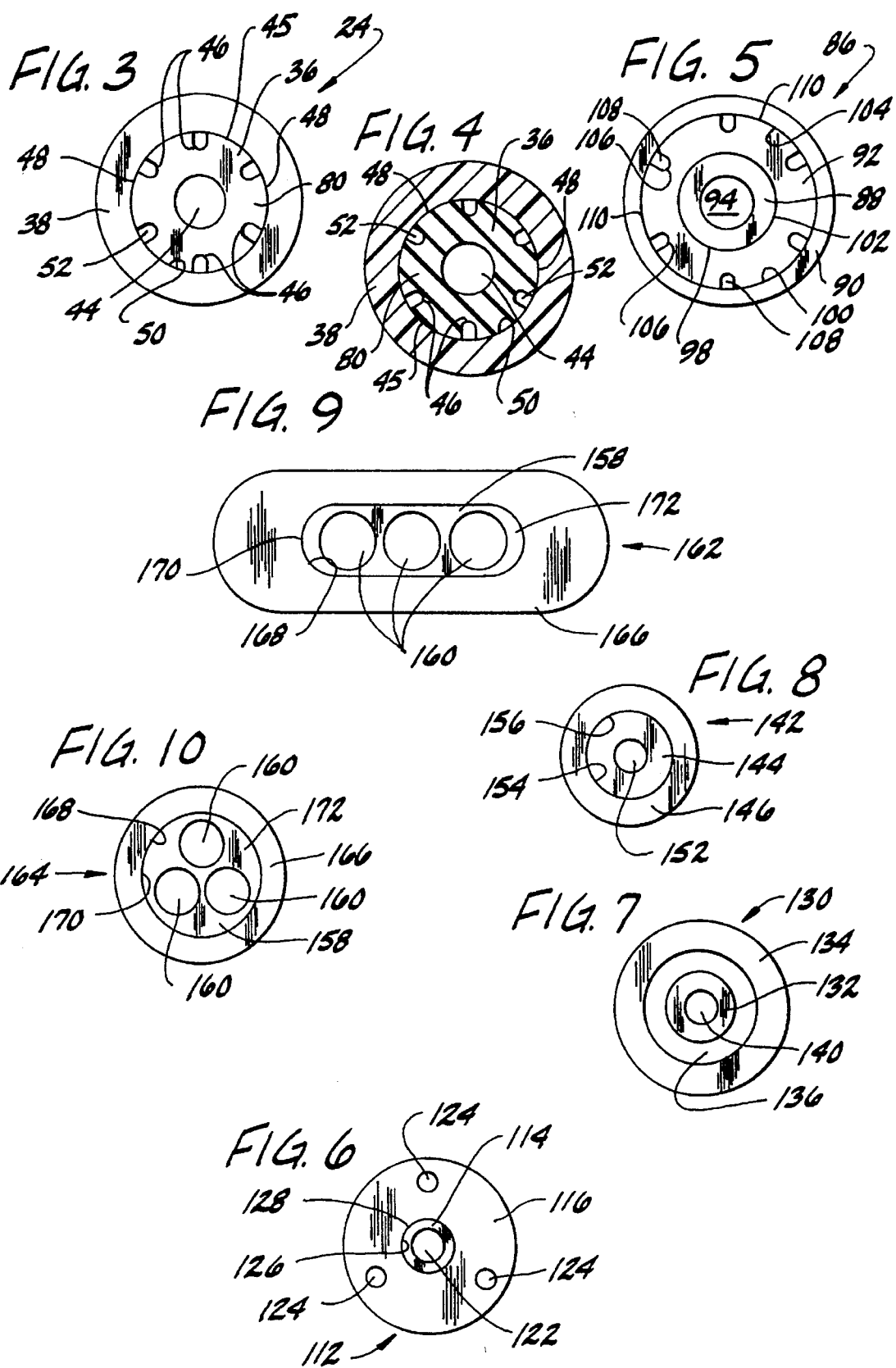

5,460,619

DISPOSABLE TUBULAR DEVICE AND METHOD

BACKGROUND OF THE INVENTION

This invention relates to disposable tubular devices of the type used with medical instruments for delivering fluid to or evacuating fluid from a patient.

Tubular devices for transporting fluids between a patient and a medical instrument are typically used by medical professionals such as physicians, dentists and dental technicians, and veterinarians for suctioning fluid from or irrigating a part of a patient's body. One such tubular device is a disposable syringe tip for an air-water dental syringe.

A typical syringe tip has a central water passageway and at least one passageway through which air may flow. The tip is typically sealingly retained in a syringe hand-piece by a retaining collar which compresses an O-ring against the tip to seal the connection between the tip and the handpiece. Between uses of the syringe, the tip must be removed from the hand-piece by wholly or partially disengaging the retaining collar. The tip is then either sterilized before reuse or discarded and replaced with a new syringe tip.

A disadvantage encountered with prior syringe tip designs is the difficulty in having a quickly detachable tip which provides a water-tight seal between the central water passageway of the tip and a water conduit of the hand-piece. In some syringes, no elastomeric seal is placed between the water conduit and the central water passageway. In such syringes, water may leak between the conduit and the tip. In other conventional syringes, O-rings are positioned between the end of the tip and the water conduit of the hand-piece. With these syringes, the O-ring is repeatedly used until the O-ring fails, which may be at an inopportune time. Also, unless the O-ring is squeezed between the hand-piece and the tip, the O-ring will not prevent leakage. Further, the force of water from the conduit tends to unseat the tip from the O-ring.

SUMMARY OF THE INVENTION

Among the several objects of this invention may be noted the provision of an improved tubular device for conveying fluid between a medical instrument and a patient; the provision of such a device which is adapted for self-sealing to a fluid conduit of the medical instrument; the provision of such a device which is easily attached to and detached from the medical instrument; the provision of such a device which is disposable; and the provision of such a device which is of relatively simple and inexpensive construction.

Generally, a disposable tubular device of this invention is adapted for releasable and sealing connection to a medical instrument for transporting fluid between a patient and the instrument. The instrument has a nipple with a fluid passageway therethrough. The device comprises a generally pliable elongate tube of resilient material extending substantially the entire length of the device and a tube-support structure extending substantially the entire length of the tube. The tube has a proximal end configured to be slidably pushed onto the nipple of the medical instrument to a position in which the nipple fits snugly inside the proximal end of the tube, a distal end, and an elongate fluid passageway extending through the tube from its proximal end to its distal end. The elongate fluid passageway is adapted to communicate with the fluid passageway of the nipple when the proximal end of the tube is on the nipple. The tube is sufficiently pliable to expand radially outwardly at its proximal end when the proximal end is pushed on the nipple and is sufficiently resilient to form a continuous seal around the nipple for sealing against fluid leakage between the nipple and the tube when fluid flows through the passageways. The tube-support structure has a stiffness greater than that of the tube and sufficient to maintain the tube in a selected operative position.

Generally, a method of making a disposable tubular device in accordance with the present invention comprises extruding a first material through a first die to form the tube and moving the tube through a second die while extruding a second material through the second die to form the tube-support structure. The second material has a durometer hardness reading which is greater than the durometer hardness reading of the first material at such temperature.

Other objects and features will be in part apparent and in part pointed out hereinafter.

BRIEF DESCRIPTION OF THE DRAWINGS

FIG. 1 is a side elevational view of a dental syringe of the present invention, with portions broken away to show detail;

FIG. 2 is a side elevational view of a syringe tip of the syringe of FIG. 1, with portions broken away to show detail;

FIG. 3 is an end elevational view of the syringe tip of FIG. 2 showing coaxial inner and outer tubes with a central water passageway through the inner tube and a plurality of air passageways defined by the inner and outer tubes;

FIG. 4 is a vertical sectional view taken along the plane of line 4—4 of FIG. 2;

FIG. 5 is an end elevational view a tubular device of the present invention similar to the syringe tip of FIGS. 2–4 but having the air passageways defined by coaxial intermediate and outer tubes;

FIG. 6 is an end elevational view of a tubular device of the present invention similar to the syringe tip of FIGS. 2–4 but having the air passageways defined entirely by the outer tubes;

FIG. 7 is an end elevational view of a tubular device of the present invention similar to the syringe tip of FIGS. 2–4 but having only one air passageway which is generally annular in cross-section and coaxial with the water passageway;

FIG. 8 is an end elevational view showing a tubular device of the present invention similar to the syringe tip of FIGS. 2–4 but having only a single fluid passageway;

FIG. 9 is an end elevational view showing a tubular device of the present invention similar to the device of FIG. 8 but having three side-by-side fluid passageways in the inner tube of the tubular device; and FIG. 10 is an end elevational view showing a tubular device of the present invention similar to the device of FIG. 9 but having three fluid passageways radially disposed in the inner tube of the tubular device.

Corresponding reference numerals indicate corresponding parts throughout the several views of the drawings.

DETAILED DESCRIPTION OF THE PREFERRED EMBODIMENT

Referring now to the drawings, and first, more particularly to FIG. 1, a medical instrument of the present invention in the form of an air-water dental syringe is indicated in its entirety by the reference numeral 20. The dental syringe 20 comprises a conventional hand-piece, generally designated 22, a disposable syringe tip, generally designated 24, and a syringe tip coupler, generally designated 26, connecting the syringe tip to the hand-piece.

The hand-piece 22 includes a first fluid (water) conduit 28 for directing a stream of water to a discharge end 30 of the hand-piece and a second fluid (air) conduit 32 for directing an air stream to the discharge end of the hand-piece. The hand-piece 22 further includes a threaded bore 34 at its discharge end 30 for threadably receiving the syringe tip coupler 26. The water and air conduits 28, 32, respectively, of the hand-piece 22 extend from pressurized sources (not shown) to the bore 34 of the hand-piece and are in fluid communication therewith.

The syringe tip 24 comprises a generally pliable elongate inner tube 36 of resilient material extending substantially the entire length of the tip and an outer tube 38, constituting an inner tube support structure, extending substantially the entire length of and surrounding the inner tube (FIG. 2). The inner tube 36 has a proximal end 40, a distal end 42, and an elongate fluid passageway 44 extending through the inner tube from its proximal end to its distal end. The inner tube has a fluted outer surface 45 with six elongate flutes 46 equally spaced about the circumference of the outer surface, and six elongate outer surface portions 48 each between adjacent flutes. The flutes 46 and outer surface portions 48 extend the length of the inner tube 36. The inner tube 36 fits snugly within the outer tube 38 and each elongate outer surface portion 48 is in continuous contact with the inner surface 50 of the outer tube generally along the entire length of the inner tube. Preferably, the inner and outer tubes 36, 38, respectively, are held together by a close friction fit between the outer surface portions 48 of the inner tube and the inner surface 50 of the outer tube. Alternatively, the tubes 36, 38 may be bonded together, e.g., by heat or with a suitable adhesive. The flutes 46 and the inner surface 50 of the outer tube 38 define six elongate air passageways 52 circumferentially disposed about the elongate fluid passageway 44 (i.e., the central water passageway) and extending substantially the length of the tube. Preferably, the inner and outer tubes 36, 38 have generally coterminous proximal and distal ends (FIG. 2). Also preferably, the syringe tip 24 has a generally uniform cross-section (FIG. 4) throughout its entire length and its proximal end 40 (FIG. 3) is substantially the same as its distal end 42. Although the flutes 46 in this embodiment are in the outer surface 45 of the inner tube 36, it is to be understood that the flutes may alternatively be formed on the inner surface 50 of the outer tube 38 and still be within the scope of the present invention.

The syringe tip coupler 26 comprises a cylindric stem 54 having first and second externally threaded surface portions 56, 58, respectively, adjacent opposite ends 60, 62 of the stem, and a central bore 64 for receiving the syringe tip 24. The first threaded surface portion 56 is threadably fitted within the threaded bore 34 of the hand-piece 22. The second threaded surface portion 58 receives a nut 66 which maintains the syringe tip 24 in the central bore 64. The stem 54 further includes a forwardly projecting nipple 65 within the central bore 64 for receiving the proximal end 40 of the inner tube 36, a rearwardly projecting nipple 68 aligned with the forwardly projecting nipple and receivable within the water conduit 28 of the hand-piece 22, and a longitudinal opening 70 through the nipples for passage of water from the water conduit through the aligned nipples and into the central water passageway 44 of the inner tube 36. The central bore 64 is in fluid communication with the air conduit 32 by way of a radially directed opening 72 in the stem 54. A first O-ring 74 is positioned generally between the stem 54 and the hand-piece 22 circumferentially about the rearwardly projecting nipple 68 for sealing against water leakage between the water conduit 30 and the stem.

The syringe tip 24 is adapted for releasable and sealing connection to the stem 54. The proximal end 40 of the inner tube 36 is configured to be slidably pushed onto the forwardly projecting nipple 65 of the stem 54 so that the nipple fits snugly inside the proximal end of the inner tube (FIG. 1). The elongate water passageway 44 of the inner tube 36 communicates with the longitudinal opening 70 of the nipple 65 when the proximal end of the tube is positioned on the forwardly projecting nipple. To this end, the inner tube 36 is sufficiently pliable so that its proximal end 40 expands radially outwardly when pushed onto the nipple 65 and sufficiently resilient to form a continuous seal around the nipple for sealing against fluid leakage between the nipple and the inner tube when water flows through the passageways 30, 44. Because the inner tube 36 seals against the nipple 65, it is unnecessary to provide an O-ring between the inner tube and nipple.

As noted above, the syringe tip 24 is releasably secured to the syringe tip coupler 26 of the medical instrument 20 by the nut 66. A second O-ring 76 is circumferentially positioned over the outer surface 78 of the outer tube 38 and abuts a forward end 62 of the stem 54 to prevent leakage of air between the tip 24 and stem. Tightening the nut 66 urges a generally cone-shaped, split collar 82 against the second O-ring 76 to hold the O-ring in place against the stem 54 and also squeezes the collar radially inwardly against the syringe tip 24 to thereby hold the syringe tip in place. A third O-ring 84 is circumferentially positioned around the stem 54 generally between the first and second threaded surface portions 56, 58, respectively, and between the nut 66 and hand-piece 22 to prevent leakage of air from between the stem and hand-piece. Preferably, the coupler 26 is configured so that the syringe tip 24 may be inserted into and removed from the stem 54 by loosening the nut 66 without the need to remove the nut.

The inner tube 36 of the syringe tip 24 is preferably made of a pliant medical grade polyvinyl chloride or other suitable synthetic resin having a durometer hardness reading between approximately 80 Shore A and 90 Shore A. Within this range, the inner tube is sufficiently pliable to seal against water leakage and sufficiently stiff to prevent the air passageways 52 from being pinched closed when the inner tube engages the nipple 65 of the stem 54 or when the syringe tip is bent to the degree shown in FIG. 2. The outer tube 38 (i.e., the tube-support structure) is preferably made of a stiffer medical grade polyvinyl chloride, having a durometer hardness reading of at least approximately 60 Shore D (most preferably 81 Shore D) and a flex modulus of at least approximately 10,000 psi (most preferably 12,000 psi). The outer tube 38 thus has a stiffness greater than that of the inner tube 36 and sufficient to maintain the entire syringe tip 24 in a selected operative position. Preferably, the outer tube 38 is sufficiently flexible to be capable of being bent by the operator to a selected operative position (FIG. 2). The outer tube 38 is also sufficiently stiff (i.e., resistant to bending) such that the force of the fluid streams passing through the tip 24 during use do not substantially alter the shape (e.g., the angle of the bend) of the tip. Because of this stiffness, a stream of air or water, or a mixed stream of both, can be directed to the specified desired location. Because the inner and outer tubes are both of polyvinyl chloride, there is an inherent adhesion between the tubes which resists movement of the inner tube relative to the outer tube. Although the tubes are preferably formed of polyvinyl chloride, it is to be understood that the tubes could be formed of other suitable resins without departing from the scope of this invention.

A disposable tubular device of the present invention (e.g., the syringe tip 24) is preferably made by a dual-extrusion method. A first material is extruded through a first die to form an inner tube 36. This die is configured such that extrusion of the first material through the first die forms an elongate tube with elongate flutes. The flutes extend along substantially the entire length of the tube. The fluted tube is then passed longitudinally through a second die while a second material is extruded through the second die and around the inner tube. The extruded tubes are then cut to length to form the tip 24. The second die is configured so that the outer tube 38 (sleeve) so formed fits snugly over the inner tube 36. The sleeve 38 constitutes a tube-support structure for maintaining the general overall shape of the inner tube 36. The flutes 46 and a portion of an inner surface 50 of the sleeve 38 define a plurality of fluid passageways 52. The first and second materials are selected so that the outer tube of the tip 24 is stiffer than the inner tube at the typical operating temperatures of the syringe (e.g., temperatures in the range of 50° F. to 110° F.).

In use, the syringe tip coupler 26 is mated with the hand-piece 22 of the dental syringe 20 as previously described. The syringe tip 24 is inserted into the central bore 64 of the coupler 26 and slidably pushed onto the forwardly projecting nipple 65 of the coupler 26 to releasably and sealably mount the tip on the medical instrument 20. Preferably, the syringe tip 24 is provided to the operator with a bend therein. The bend causes fluid to be sprayed at an angle and also helps retain the inner tube within the outer tube. The operator may vary the angle of the bend (or remove it entirely) to facilitate the spraying of fluid at a different angle. The relatively stiff outer tube 38 ensures that the force of the fluid streams passing through the tip 24 during use does not substantially alter the shape (e.g., the angle of the bend) of the tip. Because of this stiffness, a stream of air or water, or a mixed stream of both, can be directed to the specified desired location. The operator selects the fluid stream or combination of fluid streams (e.g., air, water, or an air-water mixture) to be delivered to the patient. The water stream, if selected, flows from the pressurized source through the water conduit 28 of the hand-piece into the longitudinal opening 70 of the stem 54. The water then passes into the central water passageway 28 of the syringe tip 24 mounted on the forwardly projecting nipple 65 at its proximal end 40. The water is discharged from the distal end 42 of the inner tube 36 at the desired location. The resilient inner tube 36 prevents water leakage between the forwardly projecting nipple 65 and the inner tube as long as part of the nipple is within the inner tube. Thus, the inner tube will prevent leakage even if the tip is not fully pushed onto the nipple. Also, because of the resilient inner tube 36, the tip 24 seals against the nipple even when the tip is not tightly held on the nipple. Thus, the tip may be turned or rotated on the nipple without leakage. The air stream, if selected, flows from the pressurized source through the air conduit 32 of the hand-piece 22 into the central bore 64 of the stem 54 by way of the radially directed opening 72 in the stem 54. The pressurized air passes from the central bore 64 into the air passageways 52 of the tip 24 which are in fluid communication with the central bore. The air is discharged from the distal end 42 of the syringe tip 24 to atomize the water discharged from the inner tube 36.

After use, the syringe tip 24 is removed from the coupler 26 by disengaging the tip from the nipple 65. This is done by simply loosening the nut and pulling the tip 24 from the medical instrument 20. The tip 24 is then discarded. A new syringe tip 24 can be inserted into the coupler 26 for the next use of the medical instrument 20.

An alternative embodiment of a disposable syringe tip of the present invention, generally designated 86, is shown in FIG. 5. The tip 86 comprises an inner tube 88, an outer tube 90, and an intermediate tube 92 positioned between the inner and outer tubes. Preferably, all three tubes 88, 90, 92 have coterminous proximal and distal ends and generally uniform cross-sections throughout the entire length of the tip 86. The tip 86 has a central water passageway 94 defined by the inner tube 88. The intermediate tube 92 has inner and outer surfaces 98, 100, respectively. The inner surface 98 of the intermediate tube 92 opposes the outer surface 102 of the inner tube 88 and the outer surface 100 of the intermediate tube opposes the inner surface 104 of the outer tube 90. The outer surface 100 of the intermediate tube 92 comprises a fluted surface 106 similar to the flutes 46 of the inner tube 36 of the tip in FIGS. 2–4. The flutes 106 of the intermediate tube 92 and a portion of the inner surface 104 of the outer tube 90 define air passageways 108 extending the length of the intermediate tube. In this embodiment, either or both the intermediate and outer tubes 90, 92 may be made of a generally stiff material and constitute the tube-support structure, and the inner tube 88 comprises a generally pliable elongate tube of resilient material (similar to inner tube 36) extending substantially the entire length of the tip 86. The inner tube 88 fits snugly within the intermediate tube 92. The outer surface portion 110 of the intermediate tube 92 is in continuous contact with the inner surface 104 of the outer tube 90 generally along the entire length of the tip 86. It is to be understood that the inner surface 98 of the intermediate tube 92 may be configured with the fluted surface 106, or that the outer surface 102 of the inner tube 88 or inner surface 104 of the outer tube 90 may be formed with the flutes and still be within the scope of the present invention.

Referring now to FIG. 6, another embodiment of a syringe tip of the present invention is generally designated 112. The tip 112 comprises an inner tube 114 and an outer tube 116 preferably having coterminous proximal and distal ends and generally uniform cross-sections throughout the entire length of the tip 112. A central water passageway 122 is defined by the inner tube 114, and three air passageways 124, disposed radially outwardly of the water passageway, are defined entirely by the outer tube 116. Both the water and air passageways 122, 124 of the tubes 114, 116 extend the entire length of the tip 112. In this embodiment, the outer tube 116 is made of a generally stiff material and constitutes the tube-support structure and the inner tube 114 comprises a generally pliable elongate tube of resilient material. The inner tube 114 fits snugly within the outer tube 116 and the outer surface 126 of the inner tube 114 is in continuous contact with the inner surface 128 of the outer tube 116 generally along the entire length of the tip 114. Preferably, the inner and outer tubes 114, 116 are held together by a close friction fit, and the materials of the tubes are selected for providing an inherent adhesion of the inner tube to the outer tube. Alternatively, the tubes 114, 116 may be bonded together by heat or with a suitable adhesive.

Referring to FIG. 7, another embodiment of a syringe tip of the present invention, generally designated 130, comprises an inner tube 132 and an outer tube 134 preferably having coterminous proximal and distal ends and generally uniform cross-sections throughout the entire length of the tip. The tip 130 has a central water passageway 140 defined by the inner tube 132 and an air passageway 136 formed to be generally coaxial with respect to the water passageway. To this end, the outer tube 134 is radially spaced from the inner tube 132 to create an annulus (i.e., the air passageway 136) between the inner and outer tubes extending the length of the tip 130. The inner tube 132 is retained within the outer tube 134 due to the syringe tip being bent at a region along the length of the syringe tip. In this embodiment, the outer tube 134 constitutes the generally stiff tube-support structure and the inner tube 132 comprises a generally pliable elongate tube of resilient material.

In FIG. 8, another embodiment of a tubular device, generally designated 142, comprises a generally pliable elongate inner tube 144 of resilient material and an outer tube 146 constituting the tube-support structure. Preferably, the inner and outer tubes 144, 146 have coterminous proximal and distal ends and generally uniform cross-sections throughout the entire length of the tip 142. The inner tube 144 comprises a generally pliable elongate tube of resilient material and is formed with a central single fluid passageway 152. The inner tube 144 fits snugly within the outer tube 146 which constitutes the generally stiff tube-support structure. The outer surface 154 of the inner tube 144 is in continuous contact with the inner surface 156 of the outer tube 146 generally along the entire length of the tip 142. The single passageway embodiment 142 of the tubular device is particularly useful for suctioning fluid from a patient.

As shown in FIGS. 9 and 10, other embodiments of the tubular device for conveying one or more fluids comprise a multi-lumen inner tube 158 having a plurality of coextensive passageways 160 extending the entire length of the tube. In one embodiment (FIG. 9), generally designated 162, the passageways 160 are arranged side-by-side. In the other embodiment (FIG. 10), generally indicated at 164, the passageways 160 are circumferentially disposed in the inner tube 158. The inner tube 158 of each embodiment of the tubular devices 162, 164 comprises a generally pliable elongate tube of resilient material and is surrounded by a generally stiff outer tube 166 which constitutes the tube support structure. The inner tube 158 fits snugly within the outer tube 166 and the outer surface 168 of each inner tube 158 is in continuous contact with the inner surface 170 of each outer tube 166 generally along the entire length of the tubular device 162, 164. The wall thickness of the inner tube 158 is sufficient to allow the inner tube 158 to adequately yield in order to accept mating nipples of the medical instrument (not shown) to which it connects. The multiple lumens may be used to direct multiple fluids to a patient, or to direct fluid through one lumen while evacuating fluid through another.

Although the tubular devices are described herein as being syringe tips for dental syringes, it is to be understood that tubular devices of the present invention may have uses in various other aspects of the medical field.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable tubular device adapted for releasable and sealing connection to a medical instrument for transporting fluid between a patient and the instrument, the instrument having a nipple with a fluid passageway therethrough, the device comprising a generally pliable elongate tube of resilient material extending substantially the entire length of the device and a tube-support structure extending substantially the entire length of the tube, the tube having a proximal end configured to be slidably pushed onto the nipple of the medical instrument to a position in which the nipple fits snugly inside the proximal end of the tube, a distal end, and an elongate fluid passageway extending through the tube from its proximal end to its distal end adapted to communicate with the fluid passageway of the nipple when the proximal end of the tube is on the nipple, the tube being sufficiently pliable to expand radially outwardly at its proximal end when the proximal end is pushed on the nipple and sufficiently resilient to form a continuous seal around the nipple for sealing against fluid leakage between the nipple and the tube when fluid flows through the passageways, said tube-support structure having a stiffness greater than that of the tube and sufficient to maintain the tube in a selected operative position.

2. A device as set forth in claim 1 wherein the tube comprises an inner tube and wherein the tube-support structure comprises an outer tube surrounding the inner tube.

3. A device as set forth in claim 2 wherein the outer tube has an inner surface surrounding an outer surface of the inner tube and wherein at least a portion of the outer surface of the inner tube contacts the inner surface of the outer tube.

4. A device as set forth in claim 3 wherein:
the elongate fluid passageway of the inner tube comprises a first fluid passageway for passage therethrough of a first fluid; and
the outer surface of the inner tube and the inner surface of the outer tube define an elongate second-fluid passageway extending substantially the length of the device for passage therethrough of a second fluid.

5. A device as set forth in claim 4 wherein the first-fluid passageway and second-fluid passageway are generally coaxial.

6. A device as set forth in claim 3 wherein said at least a portion of the outer surface of the inner tube contacts the inner surface of the outer tube along substantially the entire length of the outer tube.

7. A device as set forth in claim 6 wherein the inner and outer tubes are held together by a close friction fit between the inner and outer tubes.

8. A device as set forth in claim 6 wherein the inner tube comprises a multi-lumen tube having a plurality of coextensive passageways extending substantially the entire length of the device.

9. A device as set forth in claim 6 wherein the elongate fluid passageway of the inner tube comprises a first fluid passageway for passage therethrough of a first fluid, the device further comprising at least one elongate second-fluid passageway extending substantially the entire length of one of the tubes, the second-fluid passageway being defined at least in part by one of the inner and outer tubes.

10. A device as set forth in claim 6 wherein the elongate fluid passageway of the inner tube comprises a first fluid passageway for passage therethrough of a first fluid, the device further comprising a plurality of elongate second-fluid passageways extending substantially the entire length of one of the tubes, the second-fluid passageways being defined at least in part by one of the inner and outer tubes.

11. A device as set forth in claim 10 wherein the outer tube defining a multi-lumen tube comprising the second fluid passageways, the second-fluid passageways extending substantially the entire length of the outer tube and disposed radially outwardly of the first-fluid passageway.

12. A device as set forth in claim 10 wherein one of the inner and outer surfaces comprises a fluted surface having elongate flutes, the flutes extending along substantially the entire length of the tube having the fluted surface, the flutes and the other of the inner and outer surfaces defining the second-fluid passageways.

13. A device as set forth in claim 12 wherein the outer surface of the inner tube comprises the fluted surface, the flutes and the inner surface of the outer tube defining the second-fluid passageways.

14. A device as set forth in claim 6 wherein said inner tube is adhered to said outer tube.

15. A device as set forth in claim 1 wherein the tube comprises an inner tube and the elongate fluid passageway of the tube comprises a first fluid passageway through the inner tube, the device further comprising an intermediate tube surrounding the inner tube and an outer tube surrounding the intermediate tube, the intermediate tube having inner and outer surfaces, the inner surface of the intermediate tube opposing an outer surface of the inner tube and the outer surface of the intermediate tube opposing the inner surface of the outer tube, one of the inner surface of the outer tube and inner and outer surfaces of the intermediate tube comprising a fluted surface having elongate flutes, the flutes extending along substantially the entire length of the intermediate tube, the flutes and the surface opposing said one of the inner and outer surfaces of the intermediate tube defining elongate second-fluid passageways extending substantially the length of the intermediate tube for passage therethrough of a second fluid, at least one of the intermediate and outer tubes constituting said tube-support structure.

16. A device as set forth in claim 15 wherein the outer surface of the intermediate tube comprises the fluted surface, the flutes and the inner surface of the outer tube defining the second-fluid passageways.

17. A device as set forth in claim 1 wherein the tube comprises a material having a durometer hardness reading of no more than approximately 90 Shore A.

18. A disposable tubular device adapted for releasable and sealing connection to a dental instrument for delivering first and second fluids to the mouth of a patient, the instrument having a hand-piece, a nipple extending from the hand-piece, a first conduit in the hand-piece for delivering the first fluid to a discharge end of the instrument, and a second conduit in the hand-piece for delivering the second fluid to the discharge end of the instrument, the device comprising coaxial inner and outer tubes having proximal ends for connection to the discharge end of the dental instrument and distal ends for delivering the first and second fluids to the mouth of a patient, the proximal end of the inner tube being configured to be slidably pushed onto the nipple to a position in which the nipple fits snugly inside the proximal end of the inner tube, the inner tube defining an elongate first-fluid passageway extending substantially the entire length of the device from the proximal end of the inner tube to the distal end of the inner tube, the device further comprising an elongate second-fluid passageway extending substantially the entire length of one of the tubes for passage of the second fluid through the device, the second-fluid passageway being defined at least in part by one of the inner and outer tubes, the inner tube being sufficiently pliable to expand radially outwardly at its proximal end when the proximal end is pushed on the nipple and sufficiently resilient to form a continuous seal around the nipple for sealing against fluid leakage between the nipple and inner tube when the first fluid flows therethrough, the outer tube having a stiffness greater than that of the inner tube and sufficient to maintain the inner tube in a selected operative position.

19. A device as set forth in claim 18 further comprising a plurality of elongate second-fluid passageways extending substantially the entire length of one of the tubes for passage of the second fluid through the device, the second-fluid passageways being defined at least in part by one of the inner and outer tubes.

20. A device as set forth in claim 19 wherein one of the inner and outer surfaces comprises a fluted surface having elongate flutes, the flutes extending along substantially the entire length of the tube having the fluted surface, the second-fluid passages being defined in part by the flutes.

21. A device as set forth in claim 20 wherein an elongate portion of the outer surface of the inner tube contacts the inner surface of the outer tube along substantially the entire length of the outer tube.

22. A device as set forth in claim 21 wherein the outer surface of the inner tube comprises the fluted surface, the flutes and the inner surface of the outer tube defining the second-fluid passageways.

23. A device as set forth in claim 20 wherein the inner tube comprises a material having a durometer hardness reading of no more than approximately 90 Shore A, and wherein the outer tube comprises a material having a flex modulus of at least approximately 10,000 psi.

24. A device as set forth in claim 18 wherein the proximal end of the inner tube is generally coterminous with the proximal end of the outer tube and wherein the distal end of the inner tube is generally coterminous with the distal end of the outer tube.

25. A dental syringe comprising:

a hand-piece including first and second conduits for delivering water and air to a discharge end of the hand-piece;

a syringe tip for delivering pressurized water and air to the mouth of a patient comprising coaxial inner and outer tubes having proximal ends and distal ends, a water passageway through the inner tube extending substantially the entire length of the syringe tip from the proximal end of the inner tube to the distal end of the inner tube, and a plurality of air passageways;

a syringe tip coupler extending from the hand-piece for coupling the syringe tip to the hand-piece comprising a body and a nipple extending from the body for receiving the proximal end of the inner tube, the nipple having an opening therethrough in fluid communication with the first conduit for delivering water from the first conduit to the water passageway in the syringe tip, the body having an opening therethrough in communication with the second conduit for delivering air from the second conduit to the air passageways in the syringe tip; and the inner tube being configured to be slidably pushed onto the nipple to a position in which the nipple fits snugly inside the proximal end of the inner tube, being sufficiently pliable to expand radially outwardly at its proximal end when the proximal end is pushed on the nipple, and being sufficiently resilient to form a continuous seal around the nipple for sealing against fluid leakage between the nipple and the inner tube when fluid flows therethrough, the outer tube having a stiffness greater than that of the inner tube and sufficient to maintain the tip in a selected operative position.

26. A dental syringe as set forth in claim 25 wherein the outer surface of the inner tube comprises a fluted surface having elongate flutes, the flutes extending along substantially the entire length of the outer tube, the second-fluid passages being defined in part by the flutes.

* * * * *

UNITED STATES PATENT AND TRADEMARK OFFICE
CERTIFICATE OF CORRECTION

PATENT NO. : 5,460,619

DATED : October 24, 1995

INVENTOR(S) : Bernard S. Esrock

It is certified that error appears in the above-identified patent and that said Letters Patent is hereby corrected as shown below:

In column 8, Claim 11, line 62, should read "comprises a multi-lumen tube defining".

Signed and Sealed this

Nineteenth Day of March, 1996

Attest:

BRUCE LEHMAN

Attesting Officer     Commissioner of Patents and Trademarks